United States Patent

Pickett et al.

Patent Number: 6,037,059
Date of Patent: Mar. 14, 2000

[54] HIGH MOLECULAR WEIGHT DIBENZOYLRESORCINOL UV ABSORBERS, COATING COMPOSITIONS, ARTICLES AND METHOD OF MAKING

[75] Inventors: James Edward Pickett, Schenectady; Amy Kathleen Simonian, Clifton Park, both of N.Y.

[73] Assignee: General Electric Company, Schenectady, N.Y.

[21] Appl. No.: 09/177,589

[22] Filed: Oct. 23, 1998

Related U.S. Application Data

[62] Division of application No. 08/963,814, Nov. 4, 1997, Pat. No. 5,905,172, which is a division of application No. 08/762,644, Dec. 9, 1996, Pat. No. 5,763,674.

[51] Int. Cl.⁷ .............................. B32B 27/36; C08K 5/101; C07C 69/76; C07C 67/02
[52] U.S. Cl. .......................... 428/412; 524/291; 524/335; 560/107; 560/255; 568/337
[58] Field of Search ............................ 524/291; 428/412; 560/107, 255

[56] References Cited

U.S. PATENT DOCUMENTS

| | | |
|---|---|---|
| 2,900,361 | 8/1959 | Havens . |
| 3,012,063 | 12/1961 | Roller . |
| 3,075,850 | 1/1963 | Kibler et al. . |
| 3,399,237 | 8/1968 | Dressler et al. . |
| 3,505,405 | 4/1970 | Kauder . |
| 4,845,180 | 7/1989 | Henry et al. . |
| 4,911,732 | 3/1990 | Neumann et al. . |
| 5,869,185 | 2/1999 | Bahr et al. . |

OTHER PUBLICATIONS

Chemical Abstracts, vol. 77, 1972, p. 28, 62720h by M. Karvas et al.
"Coatings", vol. 105, 19186, p. 89, 116685, N. Kubota et al.
"Heterocycles", vol. 105, 1986, p. 649, 78941p, N. Kubota et al.
"Noncondensed Aromatics", vol. 91, 1979, p. 617, M. Minagawa et al.
Material Data Sheet: ADK STAB La–51 (ex LS.BO.222) from Asnhi Denka Kogyo, Tokyo, (1 page).
Claus Huth GmbH Hamburg, Mixxim PB–30, Fairmount Chemical Col., Inc. (1 page).
Mixxim BB/100, Fiarmount Chemical Co., Inc. (2 pages).
CA 103: 123103, 1984.

Primary Examiner—Veronica P. Hoke
Attorney, Agent, or Firm—Noreen C. Johnson; Douglas E. Stoner

[57] ABSTRACT

Novel dibenzoylresorcinol compositions capable of absorbing ultraviolet light having the formula

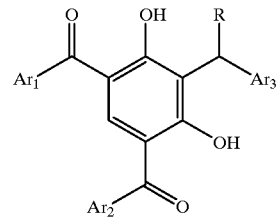

where $Ar_1$ and $Ar_2$ are independently substituted or unsubstituted monocyclic or polycyclic aryl groups, R is hydrogen, an aryl group, or a linear or branched alkyl chain having less than about 10 carbons, and $Ar_3$ is an aryl group bearing at least one hydroxyl group. Methods of making the compositions are provided. The novel dibenzoylresorcinol compositions are methylene-bridged dibenzoylresorcinol derivatives having a phenol group on the bridging methylene and are compatible in coating compositions to improve the weatherability of thermoplastic substrates.

5 Claims, No Drawings

HIGH MOLECULAR WEIGHT DIBENZOYLRESORCINOL UV ABSORBERS, COATING COMPOSITIONS, ARTICLES AND METHOD OF MAKING

This application is a division of application Ser. No. 08/963,814, filed Nov. 4, 1997 now U.S. Pat. No. 5,905,172 which is a division of application Ser. No. 08/762,644 filed Dec. 9, 1996, now U.S. Pat. No. 5,763,674 which are hereby incorporated by reference in their entireties.

FIELD OF THE INVENTION

This invention relates to novel dibenzoylresorcinol compositions capable of absorbing ultraviolet light and methods of making the compositions. Particularly, the dibenzoylresorcinol compositions are dibenzoylresorcinols coupled with a phenol on a bridging methylene group. More particularly, the invention relates to coating compositions containing the novel dibenzoylresorcinol compositions that are used to improve the weatherability of thermoplastic resins.

BACKGROUND OF THE INVENTION

Thermoplastic substrates such as polycarbonates are generally characterized by many advantageous properties which include clarity, high ductility, high heat deflection temperature, as well as dimensional stability. Many of these materials are transparent and are conventionally employed as replacements for glass in commercial applications. However, they often are susceptible to degradation by ultraviolet light. This results in unfavorable characteristics including yellowing and erosion of the substrate surface.

Recently, it is becoming more and more common for thermoplastic substrates such as polycarbonate to be employed outdoors. It is thus important to impart weatherability properties to the substrate. This is often accomplished by treating the substrate surface with a weather resistant coating material, whereby the coating material typically contains ultraviolet light absorbing agents. Weather resistant coating systems can be prepared by incorporating ultraviolet light absorbers, such as benzotriazoles and benzophenones, and hindered amine light stabilizers.

It is often discovered, however, that the ultraviolet light absorbing compounds (herein also referred to as UV absorbers), themselves, decompose upon exposure to ultraviolet light. Prolonged exposure to sunlight, moisture and thermal cycling conditions can cause yellowing, delamination and formation of microcracks in the coating material, decreasing transparency. This leads to a degradation of the favorable properties of the thermoplastic substrate which the UV absorbers are originally employed to protect. Thus, there is an ongoing need to seek new, efficient UV absorbing compounds.

Recently, 4,6-dibenzoylresorcinols (DBR) have been found to be outstanding UV absorbers in coatings due to their remarkable photostability, as described in co-pending and commonly assigned application, Ser. No. 08/669,899, titled "COATINGS USEFUL FOR ABSORBING ULTRAVIOLET LIGHT" now U.S. Pat. No. 5,869,185. Also, DBRs as bulk additives has been described by Gordon and Hudson in U.S. Pat. Nos. 2,794,052 and 2,933,553, assigned to Dow Chemical Company. However, a drawback in current compositions of DBRs is their relatively low molecular weight, i.e., molecular weight less than or equal to about 400 daltons, which leads to volatility during processing of the thermoplastic substrates or cure of the coatings. This can result in fouling of the processing equipment. Efforts to increase the molecular weight of DBR by adding substituents can result in diluting the effectiveness of the UV absorber. There is a need for novel UV absorbing compounds that retain or enhance photostability and effectiveness of the DBR chromophore while increasing the molecular weight of the compound. There is also a need to have UV absorbers with low volatility.

SUMMARY OF THE INVENTION

The instantly claimed invention satisfies this need by providing novel dibenzoylresorcinol compositions capable of absorbing ultraviolet light and methods of making the compositions. The novel dibenzoylresorcinol compositions are methylene-bridged dibenzoylresorcinol derivatives having a phenol group on the bridging methylene and are compatible in coating compositions to improve the weatherability of thermoplastic substrates. In this invention, a 4,6-dibenzoylresorcinol is converted to a claimed intermediate, a methylene acetate, which in turn is coupled with phenols to make UV absorbers of high molecular weight. The phenol can be a UV absorbing chromophore. The term "high molecular weight" as used herein for the compounds of this invention means a molecular weight greater than 400 daltons.

In a first aspect, the instant invention is directed to novel methylene-bridged dibenzoylresorcinol derivatives having a phenol group on the bridging methylene useful for absorbing ultraviolet light having the formula (II)

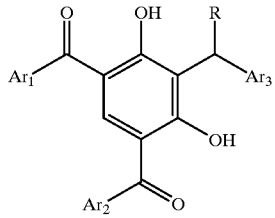

where $Ar_1$ and $Ar_2$ are independently substituted or unsubstituted monocyclic or polycyclic aryl groups, R is hydrogen, an aryl group, or a linear or branched alkyl chain having less than about 10 carbons, and $Ar_3$ is an aryl group bearing at least one hydroxyl group. $Ar_3$ can be further substituted with hydroxyl groups, alkoxy groups, benzoyl groups, substituted benzoyl groups, benzotriazoles, or triazine groups.

In a second aspect of the invention, the novel methylene-bridged dibenzoylresorcinol derivatives described above are incorporated into coating compositions. The coating compositions are defined as coatings comprising the methylene-bridged dibenzoylresorcinol derivatives and a substantially transparent matrix composition. Generally, the matrix material contains acrylics, urethanes, melamines, or mixtures thereof.

Yet another aspect of the instant invention, the above-described coatings are applied to the surface of a solid substrate thus producing a coated solid substrate having resistance to ultraviolet light. Such coated solid substrates are often referred to as weatherable substrates. Further, there are no limitations with respect to the thickness of the coatings applied to said solid substrates. They are, however, often about 0.5 to about 50 μm thick and preferably about 3 to about 10 μm thick. In the instant invention, the solid substrates that may be employed often include polymer substrates such as acrylic polymers including poly(methyl methacrylate), polyesters such as poly(ethylene terephthalate) and poly(butylene terephthalate), polyamides, polyimides, acrylonitrile-styrene copolymers, styrene-acrylonitrile-butadiene copolymers, polyvinyl chloride, polystyrene, blends of polystyrene and polyphenylene ethers, butyrates, polyethylene and the like. Thermoplastic substrates can be with or without pigments. Moreover, said solid substrates may also include metal substrates, painted surfaces, glass, ceramics and textiles. However, the coating compositions of the instant invention are preferably employed to coat polycarbonates.

Yet another aspect of the invention is a method of making the novel methylene-bridged dibenzoylresorcinol derivatives having a phenol group on the bridging methylene. Part of the method includes an intermediate step that makes a novel intermediate compound, a methylene acetate, which is then coupled with phenols to make the instantly claimed UV absorbers having high molecular weight. The method of preparing methylene-bridged dibenzoylresorcinol derivatives comprises the steps of: reacting a mixture of a 4,6-dibenzoylresorcinol and a para-aldehyde with a secondary amine catalyst and a carboxylic acid solvent at a temperature of at least 80° C. in a reaction vessel; filtering the mixture and separating methylene acetate solid from filtrate. In a second step, the methylene acetate is treated with a phenol, with or without added acid catalyst, to effect the placement of the acetate and coupling to the aromatic ring of the phenol.

Those skilled in the art will gain a further and better understanding of the present invention from the detailed description set forth below, considered in conjunction with the examples and chemical drawings accompanying and forming a part of the specification.

DETAILED DESCRIPTION OF THE INVENTION

Preparation of the novel methylene-bridged dibenzoylresorcinol derivatives having a phenol group on the bridging methylene employed in the instant invention is achieved by first making a methylene acetate intermediate having the formula

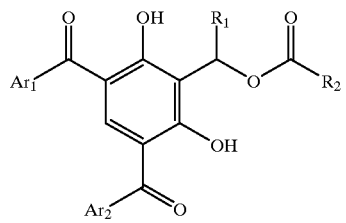

(I)

where $Ar_1$ and $Ar_2$ are independently substituted or unsubstituted monocyclic or polycyclic aryl groups and $R_1$ and $R_2$ are independently hydrogen, an aryl group, or a linear or branched alkyl chain having less than about 10 carbons. This intermediate is prepared from a dibenzoylresorcinol using a variation of the Mannich reaction described by JP 79/19,950 (CA 91:20116z). It is necessary to reduce the amine catalyst loading from 40 mole percent (as taught in the JP reference) to about 5 mole percent in order to avoid getting undesirable amounts of a diethylamine-substituted derivative. When forming the intermediate, a small amount of a methylene-bridged dimer, as shown in formula (II), is formed. This is easily removed by filtration. The isolated intermediate compound, as shown in formula (I), can be heated with an additional dibenzoylresorcinol in acetic acid solution in the presence of an acid catalyst. This results in near-quantitative formation of a desirable methylene-bridged derivative as shown in Scheme I.

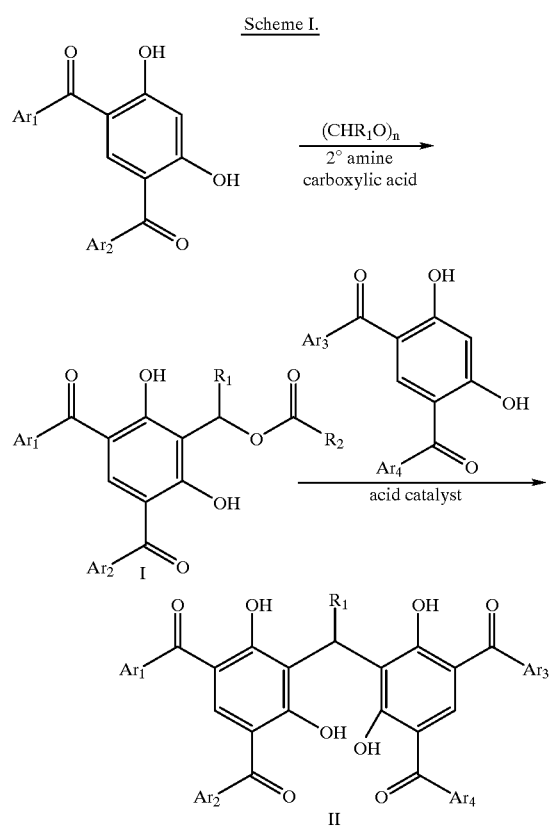

Alternative reaction conditions for the second step also have been discovered. The intermediate acetate (I) can be heated with a phenol in the absence of any added catalyst to effect coupling. The temperature for heating is between about 100–150° C. in an appropriate solvent, such as toluene or xylene. This procedure is shown in Scheme II.

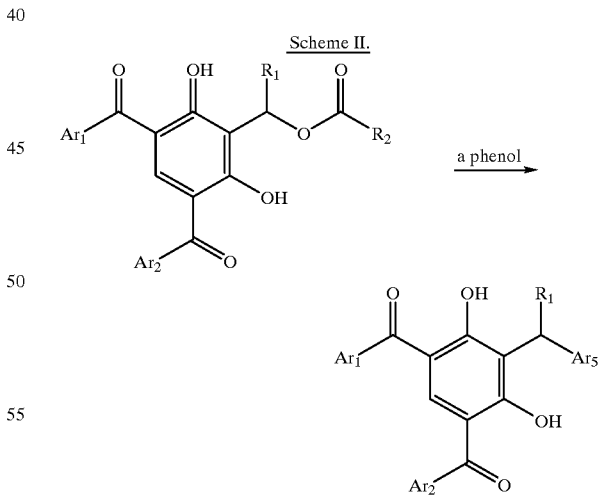

The scope of the reactions includes all possible substitutions on the phenyl rings of the starting dibenzoylresorcinol (DBR). $Ar_1$, $Ar2$, $Ar_3$, and $Ar4$ (as shown above) are independently substituted or unsubstituted mono-cyclic or polycyclic aryl groups. $Ar5$ is an aryl group bearing at least one hydroxyl group. $R_1$ is hydrogen, an aryl group, or a linear or branched alkyl chain having less than about 10 carbons.

The reaction to make the intermediate, a methylene acetate, formula I, (step 1) can be carried out in a variety of carboxylic acid solvents, such as, but not limited to, acetic acid, propionic acid, hexanoic acid, and the like. Any secondary amine catalyst may be used in an effective amount to carry out the reaction. Also, the reaction in step 1 is carried out in the presence of a para aldehyde, such as paraformaldehyde or para acetaldehyde. The temperature conditions applied to carry out the forming of the intermediate acetate (step 1) are about 80° C. or greater with a sufficient amount of time to complete the reaction.

The coupling step (step 2) from the isolated methylene acetate intermediate can be carried out in many different solvents, such as, but not limited to, methylene chloride, acetic acid, toluene and xylene. This step is carried out in the presence of a mineral acid, such as sulfuric acid, or may be completed in an organic acid used as a solvent, such as acetic acid. Coupling can also be effected in the absence of added acid catalyst. It is further part of this invention, that the DBR derivative used in step 2 to make the novel methylene-bridged dibenzoylresorcinol derivatives having a phenol group on the bridging methylene, is substituted differently from the starting DBR in step 1 used to make the intermediate compound. This yields unsymmetric DBR derivatives in the novel methylene-bridged dibenzoylresorcinol derivatives having a phenol group on the bridging methylene. The temperature conditions applied to carry out the coupling step are from about room temperature to reflux with a sufficient amount of time to complete the reaction.

It has further been discovered that the above-mentioned reaction can be performed with any phenol under uncatalyzed conditions. Dibenzoylresorcinol (DBR) can be considered a phenol, as are 2-hydroxy-4-alkoxybenzophenones; 2,2'-dihydroxy-4-alkoxybenzophenones; 2-hydroxyphenylbenzotriazoles; and 2-hydroxy-4-alkoxyphenyl triazines. These phenols not only increase the molecular weight of the dibenzoylresorcinol. They also impart additional UV absorbing properties as well as modifying the solubility of the derivative.

The preparation of the novel methylene-bridged dibenzoylresorcinol derivatives having a phenol group on the bridging methylene of the instant invention is further illustrated by the following examples. Molecular structures of all products in the examples may be confirmed by the proton and carbon-13 nuclear magnetic resonance spectroscopy and mass spectral analysis.

EXAMPLE 1

Preparation of 2-(acetoxymethyl)-4,6-dibenzoylresorcinol (the methylene acetate intermediate compound, shown in formula I'). 4,6-Dibenzoylresorcinol (63.6 grams, 200 mmol), paraformaldehyde (9 grams, 300 mmol), and diethylamine (1.0 milliliters, 10 mmol) were combined in about 65 milliliters of glacial acetic acid. The mixture was stirred and heated at about 100° C. for about 16 hours. The mixture was filtered while hot to remove some dimer of formula II' (4.3 grams, 6.7% yield). The filtrate was diluted with an additional 40 milliliters of acetic acid, cooled, and filtered to yield the methylene acetate shown in formula I': 52.0 grams, 68% yield.

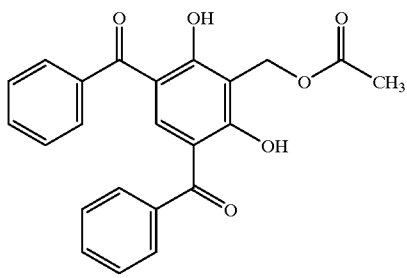

(I')

EXAMPLE 2

Preparation of Bis(2.6-dihydroxy-3,5-dibenzoylphenyl) methane. The intermediate compound of Example 1, herein referred to as Acetate, (60.45 grams, 155 mmol) and 4,6-dibenzoylresorcinol (47.7 grams, 150 mmol) and concentrated sulfuric acid (1 gram, 10 mmol) were combined in 100 milliliters of acetic acid. The mixture was stirred and heated at reflux for about 4 hours and then cooled. The resulting solid was filtered, washed with acetic acid, and dried to yield the novel dimer compound, shown in formula II': 81.81 grams, 84% yield.

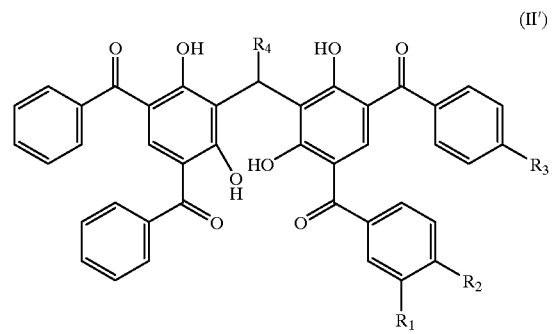

(II')

where $R_1=R_2=R_3=R_4=H$.

EXAMPLE 3

Preparation of compound III. Intermediate acetate (0.66 grams, 2 mmol) and 4-benzoyl-6-(3'-methylbenzoyl) resorcinol (0.78 grams, 2 mmol) and 3 drops of concentrated sulfuric acid were combined in 7 milliliters of glacial acetic acid. The solution was heated at reflux for 5 hours and allowed to stand at room temperature overnight. Addition of water and 2-propanol yielded orange crystals that were filtered and washed with 2-propanol. This product was slurried with hot ethanol, cooled, and filtered to yield 1.15 grams, 87% yield of light orange powder.

The formula is

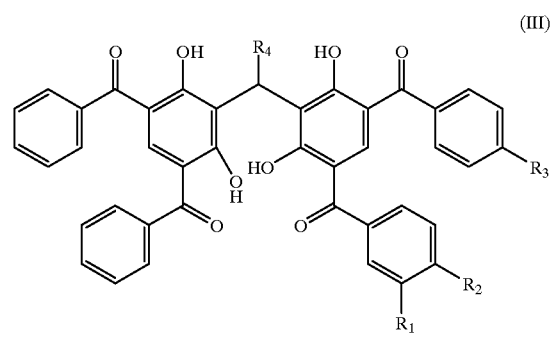

(III)

where $R_1=CH_3$; and $R_2=R_3=R_4=H$.

EXAMPLE 4

Preparation of compound IV. The procedure for compound III was carried out on 3.90 grams (10 mmol) of the intermediate acetate and 4.30 grams (10 mmol) of 4,6-di-(4-t-butylbenzoyl)resorcinol, 25 milliliters of glacial acetic acid, and 10 drops of concentrated sulfuric acid. The reaction gave 4.74 grams (62% yield) of a tan solid. The formula for compound IV is

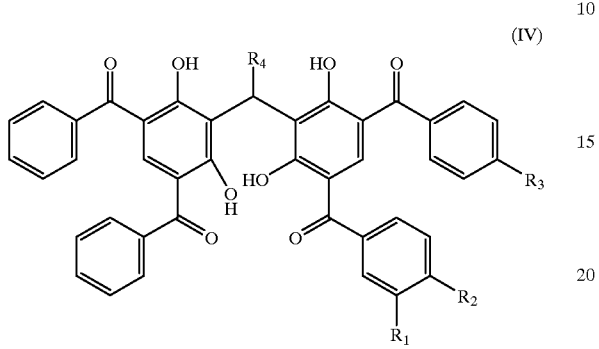

(IV)

where $R_1$=H; $R_2$=$R_3$=t-butyl; and $R_4$=H.

EXAMPLE 5

Preparation of compound V. Intermediate acetate (3.9 grams, 10 mmol) and 2,4-dihydroxybenzophenone (2.14 grams, 10 mmol) were combined in a flask with 5 milliliters of toluene, and the mixture was stirred and heated at reflux for about 12 hours. Ethanol was added to the cooled reaction mixture to produce a solid that was twice recrystallized from ethanol to give 1.72 grams (32% yield) of a light yellow powder. Nuclear Magnetic Resonance (NMR) spectroscopy revealed the product to be compound V with approximately 33% of the isomer coupled in the 3-position (position of $R_2$ in structure V). The formula for compound V is

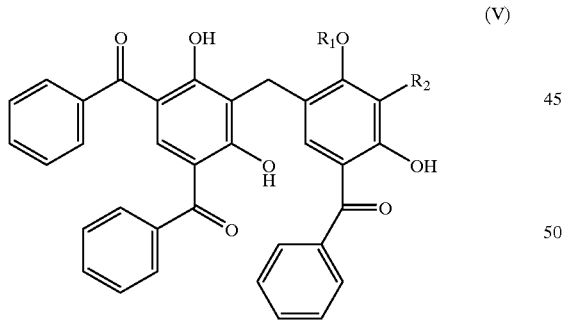

(V)

where $R_1$=H and $R_2$=H.

EXAMPLE 6

Preparation of compound VI. Intermediate acetate (1.0 gram, 2.56 mmol) and 2,4-dihydroxy-3-methylbenzophenone (0.59 grams, 2.56 mmol) were combined in a flask with 7 milliliters of toluene. The mixture was heated at reflux for about 18 hours to give a precipitate. The mixture was cooled, filtered, and the precipitate washed with toluene to give 0.85 grams (59% yield) of a light yellow solid. The formula for compound VI is

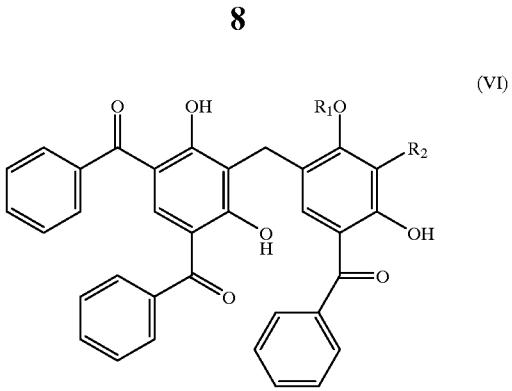

(VI)

where $R_1$=H and $R_2$=$CH_3$.

EXAMPLE 7

Preparation of compound VII. Intermediate acetate (1.0 gram, 2.56 mmol) and 2-hydroxy-4-octyloxybenzophenone (0.84 grams, 2.56 mmol) were combined in a flask with 7 milliliters of xylenes. The mixture was heated at reflux for 30 hours. The mixture was cooled and a solid precipitated upon addition of 2-propanol which was filtered and recrystallized from chloroform/ethanol to give 0.20 grams (12% yield) of a light yellow solid. Some coupling also occurred in the 3-position of the benzophenone. The formula for compound VII is

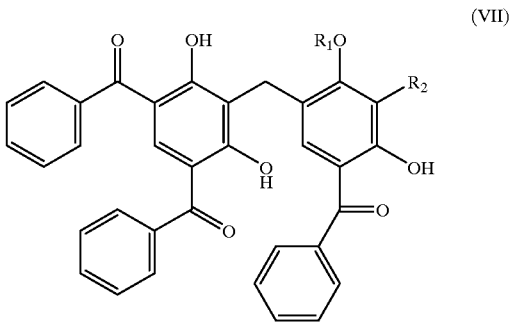

(VII)

where $R_1$=$C_8H_{17}$ and $R_2$=H.

EXAMPLE 8

Preparation of compound VIII. The procedure for compound VII was followed except that 0.625 grams (2.56 mmol) of 2,2'-dihydroxy-4-methoxybenzophenone was used in place of 2-hydroxy-4-octyloxybenzophenone. Precipitation, filtration, and washing with 2-propanol gave 0.50 grams (34% yield) of light yellow solid. NMR spectroscopy showed it to consist of approximately equal portions of structure VIII and the isomer where coupling had occurred in the 3-position of the benzophenone. The formula for compound VIII is

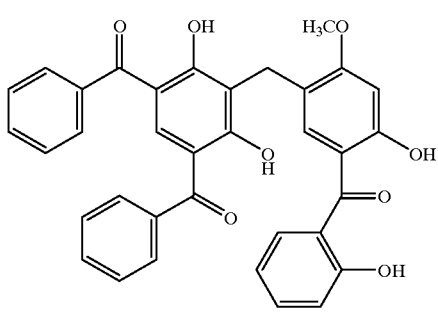

(VIII)

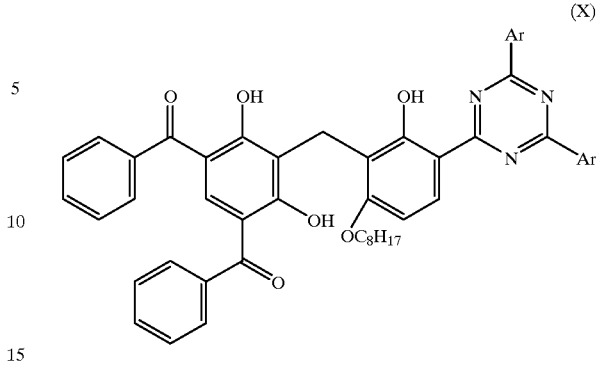

where Ar=2,4-dimethylphenyl.

EXAMPLE 11

Preparation of compound XI. Intermediate acetate (3.9 grams, 10 mmrol) and phenol (2.8 grams, 30 mmol) were combined in a flask with 5 milliliters of toluene and heated at reflux for about 12 hours. The reaction mixture was cooled and ethanol was added to precipitate the product which was filtered and twice recrystallized from ethanol/toluene to give 2.7 grams (64% yield) of a white solid. The NMR spectrum was consistent with structure XI with minor (~10%) amounts of the isomers coupled in the 3 and 4 position of the phenol. The formula for compound XI is

EXAMPLE 9

Preparation of compound IX. The procedure for compound VII was followed using 3.9 grams (10 mmol of intermediate acetate and 3.25 grams (10 mmol) of 2(2'-hydroxy-5'-t-octylphenyl)banzotriazole to yield 3.11 grams (48% yield) of a light yellow solid. The formula for compound IX is

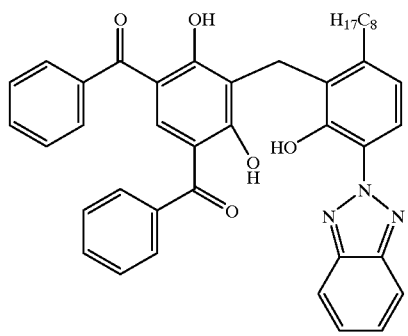

(IX)

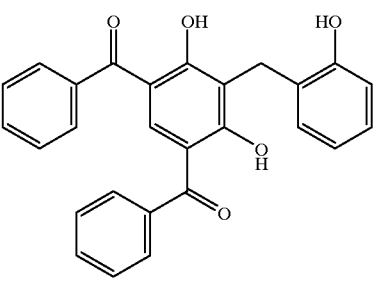

(XI)

EXAMPLE 13

Weathering of coatings containing compounds II'–XII. A solution was prepared by adding 28.15 grams of poly (methyl methacrylate) to 500 milliliters of a mixture of 85 parts of 2-methoxypropanol and 15 parts of diacetone alcohol. To 25 gram portions of this solution, 0.070 grams of one of the novel UV absorbing compound of this invention was added, mixed on a roll mill for about 12 hours, and filtered, if necessary. The solutions were then flow coated onto strips of unstabilized 15 mil Lexan® film (a registered trademark of General Electric Company), air dried, and then baked in an oven at about 105° C. for about 30 minutes. The films were then exposed in an Atlas Ci35a xenon arc Weatherometer equipped with borosilicate inner and outer films, operating at 0.77 W/m² irradiance at 340 nm in a cycle of 160 minutes light, 5 minutes dark, 15 minutes dark with water spray. This cycle applies 2.46 kJ/m² of energy at 340 nm per hour of operation. Table 1 shows the change in Yellowness index (ASTM D-1925) after 343 hours of weathering. It can be seen from Table 1 that in every case the UV absorber improved the yellowing performance relative to the uncoated control sample.

EXAMPLE 10

Preparation of compound X. Intermediate acetate (1.0 gram, 2.56 mmol) and 2,4-bis(2,4-dimethylphenyl)- 6-(2-hydroxy-4-octyloxyphenyl)-s-triazine (1.3 grams, 2.56 mmol) were combined in a flask with 5 milliliters of toluene, and the mixture was heated at reflux for about 24 hours. The mixture was cooled, precipitated by addition of 2-propanol and chloroform, filtered, and the precipitate was twice recrystallized from ethanol/toluene to give 1.23 grams (59% yield) of a light yellow solid. The NMR spectroscopy was consistent with structure (X) plus a minor amount of the product coupled at the 5-position of the 2-hydroxyphenyltriazine. The formula for compound X is

TABLE 1

WEATHERING OF COATED POLYCARBONATE FILMS.

| Additive | Delta YI at 343 Hours |
|---|---|
| uncoated (control) | 6.5 |
| II'* | 4.7 |
| III | 0.7 |
| IV | 1.1 |
| V | 1.4 |
| VI | 1.4 |
| VII* | 4.5 |
| VIII | 1.6 |
| IX | 1.5 |
| X* | 5.7 |
| XI | 2.3 |

*poorly soluble in this coating solution

EXAMPLE 14

Volatility of compounds. Thermogravimetric analysis was performed on 4,6-dibenzoylresorcinol, compound II', and Mixxim BB-100 (product of Fairmount Chemical Company), a state-of-the-art "dimeric" benzotriazole. The analysis was performed in air at 10 deg/min on a TA Instrument, TGA2950, under air flow of 55 cc/min. Compound Ia was superior to the Mixxim BB100 and the monomeric 4,6-dibenzoylresorcinol in terms of volatility as demonstrated in Table 2.

TABLE 2

VOLATILITY OF COMPOUNDS

| | | Temperature (° C.) at weight loss of | | |
|---|---|---|---|---|
| Entry | Compound | 10% | 20% | 50% |
| 1 | DBR | 250 | 267 | 275 |
| 2 | II' | 379 | 402 | 535 |
| 3 | Mixxim BB-100 | 374 | 400 | 430 |

1 = 4,6-dibenzoylresorcinol
2 = Bis(2,6-dihydroxy-3,5-dibenzoyl phenyl) methane
3 = methylene-bridged dimer of 2-(2'hydroxy-4'-octyl phenyl) benzotriazole

What is claimed:

1. A compound having the formula

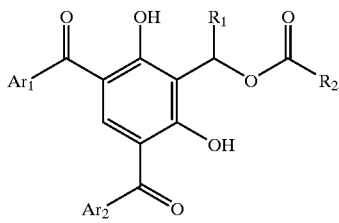

where $Ar_1$ and $Ar_2$ are independently substituted or unsubstituted monocyclic or polycyclic aryl groups and $R_1$ and $R_2$ are independently hydrogen, an aryl group, or a linear or branched alkyl chain having less than about 10 carbons.

2. A compound according to claim 1 where said compound is used to make a methylene-bridged dibenzoylresorcinol derivative.

3. A coating comprising:

a compound useful for absorbing ultraviolet light having the formula

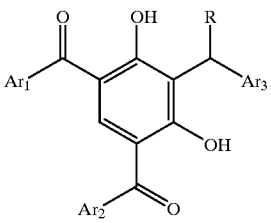

where $Ar_1$ and $Ar_2$ are independently substituted or unsubstituted monocyclic or polycyclic aryl groups, R is hydrogen, an aryl group, or a linear or branched alkyl chain having less than about 10 carbons, and $Ar_3$ is an aryl group bearing at least one hydroxyl group; and a substantially transparent matrix composition.

4. A coating according to claim 3 where said transparent matrix is selected from the group consisting of acrylics, urethanes, melamines, and mixtures thereof.

5. A solid substrate with a coating composition applied thereon wherein said coating composition comprises:

a compound useful for absorbing ultraviolet light having the formula

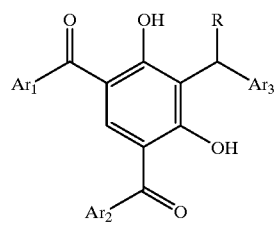

where $Ar_1$ and $Ar_2$ are independently substituted or unsubstituted monocyclic or polycyclic aryl groups, R is hydrogen, an aryl group, or a linear or branched alkyl chain having less than about 10 carbons, and $Ar_3$ is an aryl group bearing at least one hydroxyl group; and a substantially transparent matrix composition.

* * * * *